United States Patent
Skirble et al.

(10) Patent No.: US 9,619,617 B2
(45) Date of Patent: Apr. 11, 2017

(54) SYSTEM AND METHOD FOR DETERMINING A LOCATION AND A STATUS OF AN ASSET

(75) Inventors: Barry Skirble, Allison Park, PA (US); Paul Molingowski, Allison Park, PA (US)

(73) Assignee: Aethon, Inc., Pittsburgh, PA (US)

( * ) Notice: Subject to any disclaimer, the term of this patent is extended or adjusted under 35 U.S.C. 154(b) by 389 days.

(21) Appl. No.: 12/856,040

(22) Filed: Aug. 13, 2010

(65) Prior Publication Data

US 2011/0037565 A1    Feb. 17, 2011

Related U.S. Application Data

(60) Provisional application No. 61/233,758, filed on Aug. 13, 2009.

(51) Int. Cl.
| | |
|---|---|
| G08B 5/22 | (2006.01) |
| G08B 25/00 | (2006.01) |
| G06F 19/00 | (2011.01) |
| G06Q 10/08 | (2012.01) |

(52) U.S. Cl.
CPC ......... *G06F 19/327* (2013.01); *G06Q 10/087* (2013.01)

(58) Field of Classification Search
CPC ........ G06K 2017/0045; G07C 9/00111; G08B 3/1083

USPC .... 340/8.1, 10.1–10.6, 539.12, 573.1; 901/1, 901/35, 44, 46
See application file for complete search history.

(56) References Cited

U.S. PATENT DOCUMENTS

| | | | |
|---|---|---|---|
| 7,504,949 B1* | 3/2009 | Rouaix et al. | 340/572.1 |
| 2004/0193449 A1* | 9/2004 | Wildman | G06Q 50/22 705/2 |
| 2006/0079994 A1* | 4/2006 | Chu et al. | 700/231 |
| 2007/0080801 A1* | 4/2007 | Weismiller et al. | 340/539.13 |
| 2008/0284600 A1* | 11/2008 | Drzaic et al. | 340/572.1 |
| 2008/0316045 A1* | 12/2008 | Sriharto | G06Q 50/22 340/10.1 |
| 2009/0021351 A1* | 1/2009 | Beniyama | G05D 1/024 340/10.1 |
| 2009/0327102 A1* | 12/2009 | Maniar | G06F 19/327 705/28 |

* cited by examiner

*Primary Examiner* — George Bugg
*Assistant Examiner* — Anthony D Afrifa-Kyei
(74) *Attorney, Agent, or Firm* — Buchanan Ingersoll & Rooney PC

(57) ABSTRACT

A method. The method includes, at a computing system, receiving information associated with an asset. The method also includes determining a location of the asset based on the received information, and determining a status of the asset based on the received information and/or the determined location of the asset. The determining of the location and the determining of the status are performed by the computing system.

12 Claims, 3 Drawing Sheets

SYSTEM AND METHOD FOR DETERMINING A LOCATION AND A STATUS OF AN ASSET

CROSS-REFERENCE TO RELATED APPLICATION

This application claims the benefit under 35 U.S.C. §119(e) of the earlier filing date of U.S. Provisional Patent Application No. 61/233,758 filed on Aug. 13, 2009.

BACKGROUND

This application discloses an invention which is related, generally and in various embodiments, to a system and method for determining a location and a status of an asset.

In the health care industry, in order to realize high quality patient care, it is important to have the appropriate medical equipment in the appropriate place, at the appropriate time and in the appropriate condition. In the hospital environment, the tasks of locating the equipment and determining the status of the equipment are typically performed by hospital personnel. The hospital personnel generally walk throughout the entire facility, including patient rooms, to determine the respective locations of various types of medical equipment. Additionally, the hospital personnel are often utilized to determine the status of the equipment. For example, after locating a given piece of medical equipment, the personnel may determine whether or not the equipment is in use, and if the equipment is not in use, whether or not the equipment is available for use.

The manual process of locating and determining the status of medical equipment is relatively expensive and inefficient, and medical equipment is regularly lost, stolen, hidden, or not serviced when required. Due to the nature of the manual process, status data regarding the medical equipment is usually collected only once per day, and thus the accuracy, timeliness, and value of the status data is severely limited. The manual process can compromise patient privacy and can contribute to the spread of infections throughout the environment.

BRIEF DESCRIPTION OF THE DRAWINGS

Various embodiments of the invention are described herein in by way of example in conjunction with the following figures, wherein like reference characters designate the same or similar elements.

DETAILED DESCRIPTION

It is to be understood that at least some of the figures and descriptions of the invention have been simplified to illustrate elements that are relevant for a clear understanding of the invention, while eliminating, for purposes of clarity, other elements that those of ordinary skill in the art will appreciate may also comprise a portion of the invention. However, because such elements are well known in the art, and because they do not facilitate a better understanding of the invention, a description of such elements is not provided herein.

Figure 1:
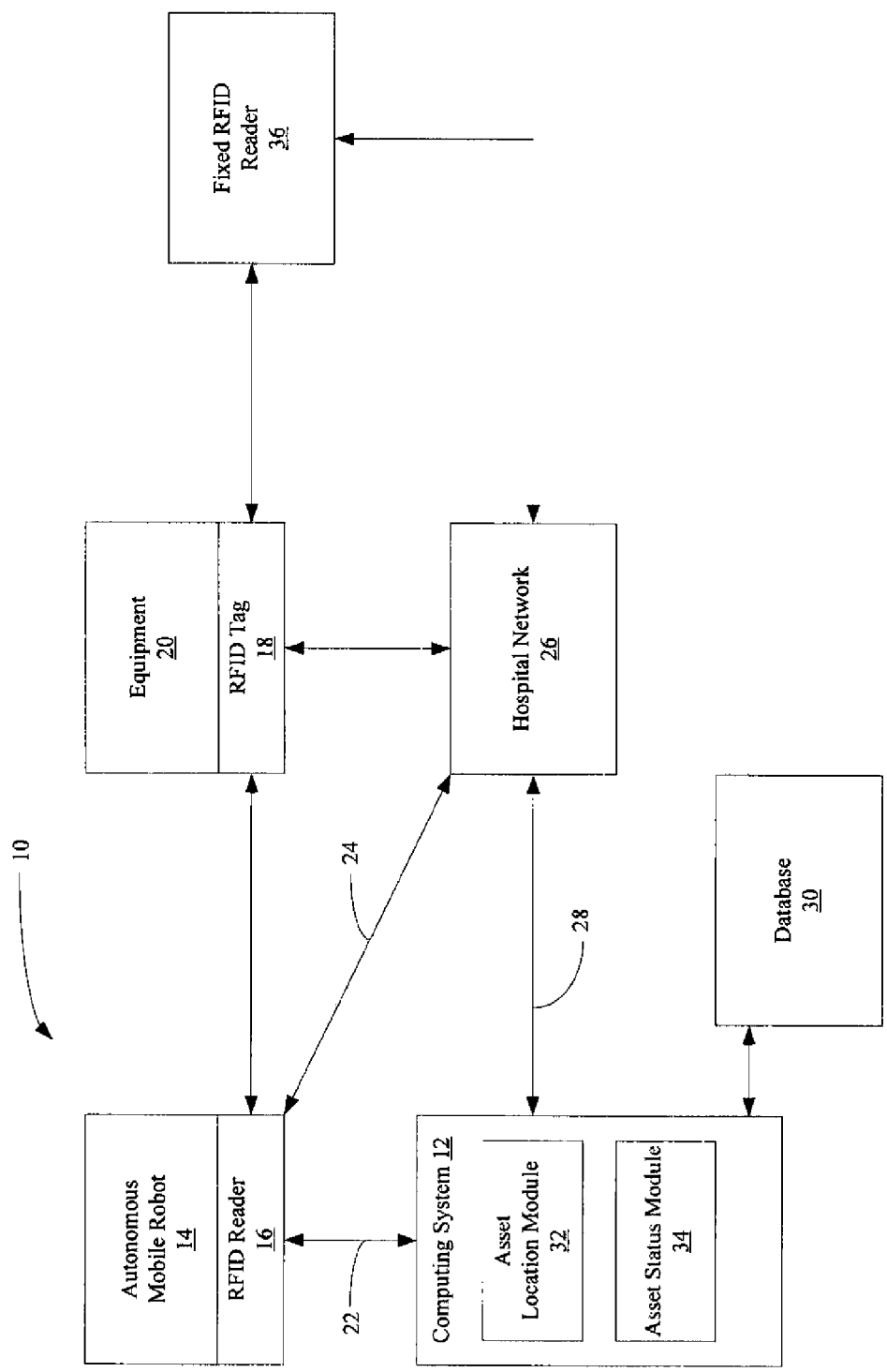
FIG. 1 illustrates various embodiments of a system.

FIG. 1 illustrates various embodiments of a system 10. As explained in more detail hereinafter, the system 10 may be utilized to determine the location and status of one or more assets (e.g., medical equipment) throughout a facility. Although the system 10 may be utilized to determine the location and status of any type of asset in any type of facility, for purposes of simplicity, the system 10 will be described in the context of its use with medical equipment.

The system 10 includes a computing system 12. The computing system 12 may be any suitable type of computing system, and various embodiments of the computing system 12 are described with respect to FIG. 2.

Figure 2:
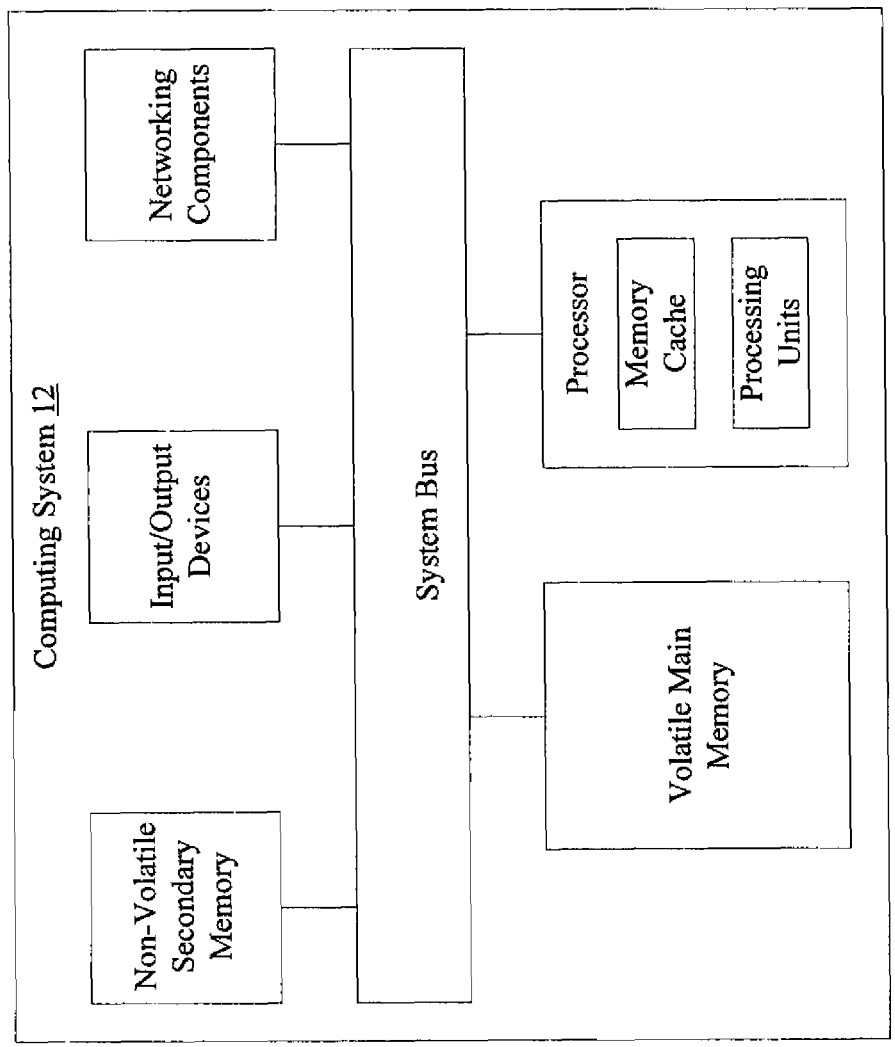
FIG. 2 illustrates various embodiments of a computing system of the system of FIG. 1.

FIG. 2 illustrates various embodiments of the computing system 12 of FIG. 1. The computing system 12 may be embodied as one or more computing devices (e.g., servers), and includes networking components such as Ethernet adapters, non-volatile secondary memory such as magnetic or optical storage devices, input/output devices such as keyboards and visual displays, volatile main memory, and a processor. Each of these components may be communicably connected via a common system bus. The processor includes processing units and on-chip storage devices such as memory caches.

According to various embodiments, the computing system 12 includes one or more modules (described in more detail hereinbelow) which are implemented in software, and the software is stored in non-volatile memory devices while not in use. When the software is needed, the software is loaded into volatile main memory. After the software is loaded into volatile main memory, the processor reads software instructions from volatile main memory and performs useful operations by executing sequences of the software instructions on data which is read into the processor from volatile main memory. Upon completion of the useful operations, the processor writes certain data results to volatile main memory. Additional description of various embodiments of the computing system 12 will be set forth hereinbelow.

Returning to FIG. 1, according to various embodiments, the system 10 also includes an autonomous mobile robot 14 communicably connected to the computing system 12. In general, the autonomous mobile robot 14 may be any suitable type of autonomous mobile robot. For example, according to various embodiments, the autonomous mobile robot 14 may be embodied as an autonomous mobile robot similar to those described in any of the following: U.S. Pat. Nos. 6,046,565; 7,100,725; 7,431,115; U.S. Patent Publication 2007/0129849; and U.S. Patent Publication 2007/0112461.

The autonomous mobile robot 14 has a radio-frequency identification (RFID) reader 16 connected thereto, and the RFID reader 16 may be wirelessly connected to an RFID tag 18 which is connected to a piece of medical equipment 20. The RFID tag 18 may be embodied as a passive RFID tag or an active RFID tag, and may be connected to the piece of medical equipment 20 in any suitable manner. For example, the RFID tag 18 may be mounted to a surface of the piece of medical equipment 20. According to various embodiments, each RFID tag 18 has a unique tag number associated therewith. The respective pieces of medical equipment 20 may be any suitable type of medical equipment, and may include different types of medical equipment.

In general, the RFID reader 16 and the RFID tag 18 may be wirelessly connected when the RFID reader 16 and the RFID tag 18 are within the vicinity of one another. A distance associated with the vicinity can vary depending on the characteristics of the RFID reader 16 and the RFID tag 18, and any materials positioned between the RFID reader 16 and the RFID tag 18. Although only one autonomous mobile robot 14 is shown in FIG. 1, it will be appreciated that the system 10 may include any number of autonomous mobile robots 14. Similarly, although only one RFID tag 18 and one piece of associated medical equipment 20 is shown in FIG. 1, it will be appreciated that a given RFID reader 16 may be wirelessly connected to any number of RFID tags 18, and by extension, to any number of pieces of medical equipment 20.

As shown in FIG. 1, the computing system 12 is communicably connected to the autonomous mobile robot 14 via a wireless communication link 22. According to other embodiments, the computing system 12 may be communicably connected to the autonomous mobile robot 14 via a wireless communication link 24, a hospital network 26, and a communication link 28. The communication link 28 which communicably connects the computing system 12 and the hospital network 26 may include any combination of wireless and/or wired pathways. The hospital network 26 may include any type of delivery system including, but not limited to, a local area network (e.g., Ethernet), a wide area network (e.g. the Internet and/or World Wide Web), a telephone network (e.g., analog, digital, wired, wireless, PSTN, ISDN, GSM, GPRS, and/or xDSL), a packet-switched network, a radio network, a television network, a cable network, a satellite network, and/or any other wired or wireless communications network configured to carry data. The hospital network 26 may include elements, such as, for example, intermediate nodes, proxy servers, routers, switches, and adapters configured to direct and/or deliver data. In general, the system 10 may be structured and arranged to communicate with the hospital network 26 using various communication protocols (e.g., HTTP, TCP/IP, UDP, WAP, WiFi, Bluetooth) and/or to operate within or in concert with one or more other communications systems.

As shown in FIG. 1, the computing system 12 is communicably connected to a database 30. According to various embodiments, the database 30 is integral to the computing system 12. According to other embodiments, the database 30 is separate from the computing system 12. The database 30 is configured to include information regarding the RFID tags 18, the medical equipment 20, and patient data. The patient data may include information gathered during the patient admission process, during the patient's stay at the facility, during the patient discharge process, etc. In general, the database 30 associates a given RFID tag 18 with the piece of equipment 20 to which it is connected, and may also associate the piece of equipment 20 with a given patient. Thus, the database 30 may associate one or more pieces of equipment 20 with a given patient.

The computing system 12 also includes an asset location module 32 and an asset status module 34. The asset location module 32 is configured to determine the location of an asset (e.g., medical equipment 20) in the facility based on information received from the RFID tags 18 via the RFID reader 16 and/or the autonomous mobile robot 14. The asset status module 34 is configured to determine the status of an asset (e.g., medical equipment 20) based on information received from the RFID tags 18 via the RFID reader 16 and/or the autonomous mobile robot 14, and from information from the database 30.

According to various embodiments, as the autonomous mobile robot 14 navigates throughout the facility, the RFID reader 16 communicates with RFID tags 18 connected to medical equipment 20. The information gathered by the RFID reader 16 from this process is communicated to the autonomous mobile robot 14, which in turn communicates the gathered information to the computing system 12. The gathered information may be communicated to the computing system 12 immediately upon receipt, stored for some amount of time before being communicated to the computing system 12, or a combination thereof. The asset location module 32 of the computing system 12 utilizes the communicated information to determine the respective locations of the various assets associated with the RFID tag information. The asset location module 32 may also update the database 30 to reflect the location of the assets and to plot the location of the assets (e.g., medical equipment 20) on a map stored at the computing system 12. The asset status module 34 may then analyze the information in the database 30 and determines the status of the respective assets (e.g., medical equipment 20). According to various embodiments, the status of a given piece of medical equipment 20 may be determined to be "in use", "not in use and available for use", or "not in use and not available for use".

In general, the asset status module 34 may determine the status of the medical equipment 20 on a periodic basis, whenever there is a change in any of the data associated with the medical equipment 20, and combinations thereof. For example, when a patient is discharged from the facility, the asset status module 34 may automatically change the status of a piece of medical equipment 20 associated with the patient from "in use" to "not in use and not available for use". Once the medical equipment 20 is cleaned, sterilized, reset, etc., the asset status module 34 may automatically change the status of the medical equipment 20 from "not in use and not available for use" to "not in use and available for use".

The modules 32, 34 are communicably connected to the processor of the computing system 12 and may be implemented in hardware, firmware, software and combinations thereof. For embodiments utilizing software, the software may utilize any suitable computer language (e.g., C, C++, Java, JavaScript, Visual Basic, VBScript, Delphi) and may be embodied permanently or temporarily in any type of machine, component, physical or virtual equipment, storage medium, or propagated signal capable of delivering instructions to a device. The modules 32, 34 (e.g., software application, computer program) may be stored on a computer-readable medium (e.g., disk, device, and/or propagated signal) such that when a computer reads the medium, the functions described herein are performed.

According to various embodiments, the modules 32, 34 may reside at a computing device of the computing system 12, other devices within the system 10, or combinations thereof. For embodiments where the computing system 10 includes more than one computing device, the modules 32, 34 may be distributed across a plurality of computing devices. According to various embodiments, the functionality of the modules 32, 34 may be combined into fewer modules (e.g., a single module).

As shown in FIG. 1, according to various embodiments, the system 10 may also include one or more fixed RFID readers 36 communicably connected to the computing system 12. Although not required, the fixed RFID readers 36 may be positioned throughout the facility in areas where the autonomous mobile robots 14 may not routinely navigate. For such embodiments, when a given RFID tag 18 connected to a given piece of medical equipment 20 comes within the vicinity of a given fixed RFID reader 36, the RFID reader 36 captures information from the RFID tag 18 and forwards the information to the computing system 12, either directly or via the hospital network 26.

Figure 3:
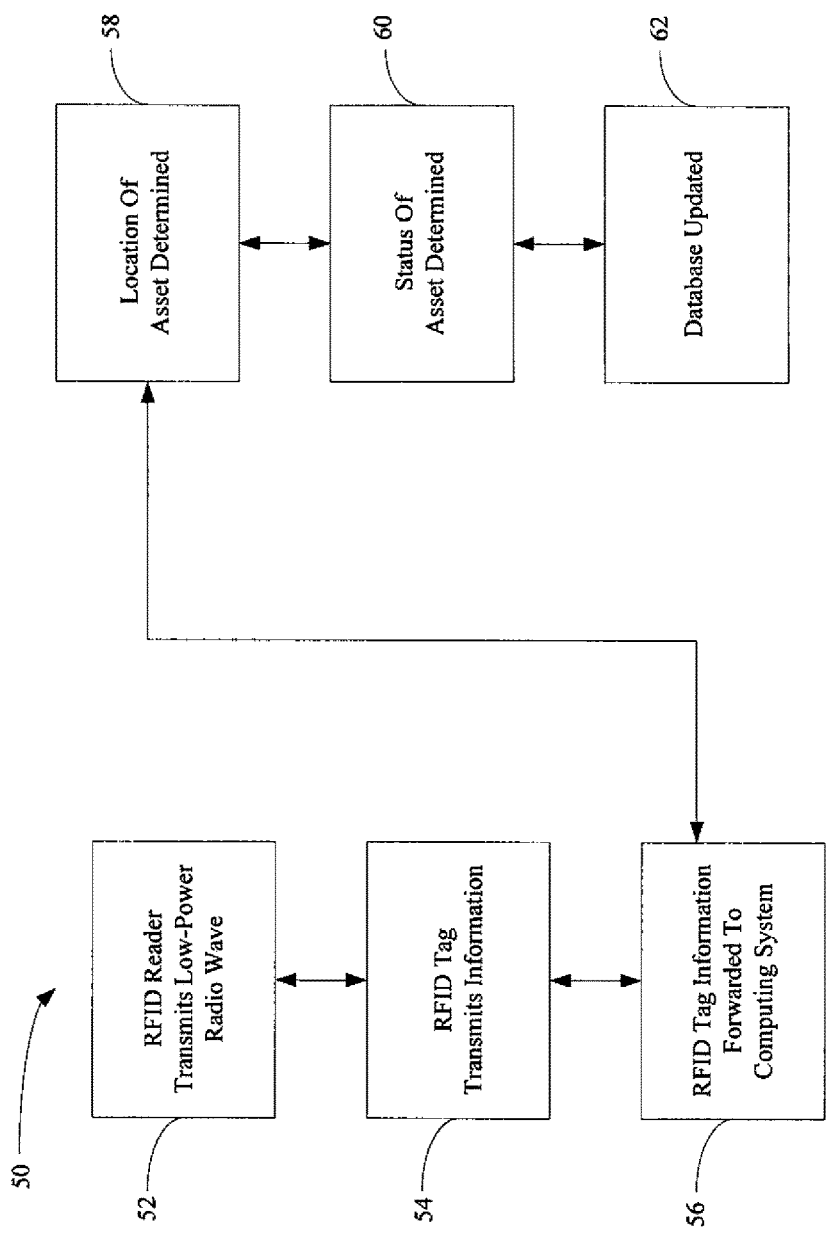
FIG. 3 illustrates various embodiments of a method.

FIG. 3 illustrates various embodiments of a method 50. As described in more detail hereinafter, the method 50 may be utilized to determine the location and status of one or more assets (e.g., medical equipment) throughout a facility. The method 50 is implemented at least in part by a computing device, and may be implemented by the system 10 of FIG. 1. For purposes of simplicity, the method 50 will be described in the context of medical equipment and being implemented by the system 10 of FIG. 1. However, it will be appreciated that the method 50 may be utilized to determine a location and status of a variety of different assets in a variety of different facilities.

Prior to the start of the process, the database 30 is populated with information which associates a given RFID tag 18 with a given piece of medical equipment 20, and also associates one or more pieces of medical equipment 20 with a given patient. For example, the unique tag number of a given RFID tag 18 is utilized to associate the RFID tag 18 with a piece of medical equipment 20 to which the RFID tag 18 is connected. Similarly, the medical equipment 20 located in a given room may be associated with a patient assigned to the room.

The process starts at block 52, where the RFID reader 16 transmits a low-power radio wave. The low-power radio wave may be utilized to power up a passive RFID tag 18 which comes in the range of the RFID reader 16. The passive RFID tag 18 may come within the range of the RFID reader 16 while the autonomous mobile robot 14 is traveling throughout a facility or when the autonomous mobile robot 14 is stationary. For example, the passive RFID tag 18 may come within the range of the RFID reader 16 when a traveling autonomous mobile robot 14 passes a stationary piece of medical equipment 20, when a traveling autonomous mobile robot 14 and a traveling piece of medical equipment 20 pass one another, or when a traveling piece of medical equipment 20 passes a stationary autonomous mobile robot 14.

From block 52, the process advances to block 54, where the passive RFID tag 18 comes within the range of the RFID reader 16. The low-power radio wave emitted by the RFID reader 16 operates to power up the passive RFID tag 18, and the passive RFID tag 18 transmits RFID tag information. The RFID tag information indicates the unique tag number of the RFID tag 18.

For embodiments where the RFID tag 18 is an active RFID tag, the process described at blocks 52-54 is somewhat different. The active RFID tag 18 has an integral power source and thereby is able to power up without receiving the low-power radio wave transmitted by the RFID reader 16 at block 52. For such embodiments, the active RFID tag 18 automatically transmits RFID tag information on a periodic basis.

From block 54, the process advances to block 56, where the RFID tag information transmitted from the RFID tag 18 is received by the RFID reader 16 when the RFID reader 16 comes within range of the RFID tag 18. The RFID reader 16 communicates the received RFID tag information to the autonomous mobile robot 14, which in turn communicates the RFID tag information to the computing system 12. According to various embodiments, the RFID tag information is communicated to the computing system 12 immediately upon receipt by the autonomous mobile robot 14. According to other embodiments, received RFID tag information may be stored at the autonomous mobile robot 14, then communicated to the computing system 12 at a later time. The RFID tag information may be communicated from the autonomous mobile robot 14 to the computing system 12 via the wireless communication link 22, or via the wireless communication link 24 and the hospital network 26.

From block 56, the process advances to block 58, where RFID tag information is received at the computing system 12, and is utilized by the asset location module 32 to determine the location of medical equipment 20 to which the RFID tag 18 is connected. For embodiments where the RFID tag information is communicated to the computing system 12 via the RFID reader 16, the asset location module 32 may determine the location of the asset by determining the location of the RFID tag 18 associated with the asset relative to a determined location of the autonomous mobile robot 14. The location of the autonomous mobile robot 14 may be determined on a continuous or periodic basis. For embodiments, where the RFID tag information is communicated to the computing system 12 via the fixed RFID reader 36, the asset location module 32 may determine the location of the asset by determining the location of the RFID tag 18 associated with the asset relative to a known location of the fixed RFID reader 36. The asset location module 32 may utilize the RFID tag information to update the database 30, and may also use the RFID tag information to update a map which is stored at the computing system 14, where the map indicates the determined location of the medical equipment 20.

From block 58, the process advances to block 60, where the asset status module 34 is utilized to determine the status of medical equipment 20 to which the RFID tag 18 is connected. As described hereinabove, the asset status module 34 may utilize the RFID tag information, as well as the information (e.g., patient data) in the database 30, to determine the status of the medical equipment 20.

From block 60, the process advances to block 62, where the computing system 12 updates the equipment location and status information stored in the database 30. The process described at blocks 52-62 may be repeated any number of times. In addition, at any time during the process described at blocks 52-62, the computing system 12 may receive information (e.g., patient data) from the hospital network 26 and utilize the information to update data stored in the database 30.

Nothing in the above description is meant to limit the invention to any specific materials, geometry, or orientation of elements. Many part/orientation substitutions are contemplated within the scope of the invention and will be apparent to those skilled in the art. The embodiments described herein were presented by way of example only and should not be used to limit the scope of the invention.

Although the invention has been described in terms of particular embodiments in this application, one of ordinary skill in the art, in light of the teachings herein, can generate additional embodiments and modifications without departing from the spirit of, or exceeding the scope of, the described invention. Accordingly, it is understood that the drawings and the descriptions herein are proffered only to facilitate comprehension of the invention and should not be construed to limit the scope thereof.

What is claimed is:

1. A method, comprising:
   at a computing system, receiving patient information associated with an asset via a hospital network and information from a RFID tag connected to the asset;
   populating a database with data associating the RFID tag with the asset and associating the asset with a patient;
   determining a location of the asset, wherein determining the location is performed by the computing system and comprises:
   continuously determining a location of an autonomous mobile robot; and based directly on the determined location of the autonomous mobile robot,
determining a location of the RFID tag relative to the determined location of the autonomous mobile robot;
determining a status of the asset based on the following:
the received patient information; and
the determined location of the asset, wherein determining the status is performed by the computing system;
wherein determining the status of the asset comprises determining the following:
that the asset is in use;
that the asset is not in use and is not available for use; and
that the asset is not in use and available for use;
wherein when the patient is discharged, the status of the asset associated with the patient automatically changes from in use to not in use and not available for use; and
wherein when the asset is at least one of cleaned, sterilized, and reset, the status of the asset automatically changes from not in use and not available for use to not in use and available for use; and
utilizing the patient information received from the hospital network to update the data stored in the database.

2. The method of claim 1, wherein determining the location of the RFID tag comprises determining a location of a passive RFID tag associated with the asset.

3. The method of claim 1, wherein determining the location of the RFID tag comprises determining a location of an active RFID tag associated with the asset.

4. The method of claim 1, wherein determining the location of the RFID tag comprises determining the location of the RFID tag relative to a location of a RFID reader.

5. The method of claim 1, wherein determining the location of the RFID tag comprises determining the location of the RFID tag relative to a location of a fixed RFID reader.

6. The method of claim 1, further comprising updating a map to indicate the determined location of the asset, wherein the updating is performed by the computing system.

7. The method of claim 1, further comprising storing at least one of the following in a database:
information representative of the determined location of the asset; and
information representative of the determined status of the asset, wherein the storing is performed by the computing system.

8. The method of claim 7, further comprising updating the information stored in the database, wherein the updating is performed by the computing system.

9. A system, comprising:
an autonomous mobile robot;
a computing system communicably connected to the autonomous mobile robot via a hospital network, wherein the computing system comprises:
a processor;
a storage device communicably connected to the processor;
an asset location module communicably connected to the processor, wherein the asset location module is configured to determine a location of an asset based on:
a continuously determined location of the autonomous mobile robot; and
a determined location of an RFID tag relative to the determined location of the autonomous mobile robot, wherein the RFID tag is connected to the asset; and
an asset status module communicably connected to the processor, wherein the asset status module is configured to determine a status of an asset based on:
the determined location of the asset; and
patient information associated with the asset; and
a database populated with data associating the RFID tag with the asset and associating the asset with a patient;
wherein determining the status of the asset comprises determining the following:
that the asset is in use;
that the asset is not in use and is not available for use; and
that the asset is not in use and available for use;
wherein when a patient is discharged, the status module is configured to automatically change the status of the asset associated with the patient from in use to not in use and not available for use;
wherein when the asset is at least one of cleaned, sterilized, and reset, the status module is configured to automatically change the status of the asset from not in use and not available for use to not in use and available for use; and
wherein the computer system is capable of receiving the patient information, in part, from the hospital network to update the data stored in the database.

10. The system of claim 9, wherein the autonomous mobile robot is communicably connected to the computing system via a wireless communication link.

11. The system of claim 9, further comprising an RFID reader connected to the autonomous mobile robot.

12. The system of claim 9, further comprising a fixed RFID reader communicably connected to the computing system.

* * * * *